United States Patent [19]

Burton et al.

[11] Patent Number: 4,909,785
[45] Date of Patent: Mar. 20, 1990

[54] METHOD FOR VALVING BODY FLUIDS

[75] Inventors: John H. Burton, Minnetonka; Eric P. Berg, Woodbury; Bradford G. Staehle, Minnetonka, all of Minn.; Frank B. Scott, Houston, Tex.

[73] Assignee: American Medical Systems, Inc., Minnetonka, Minn.

[21] Appl. No.: 267,748

[22] Filed: Nov. 2, 1988

Related U.S. Application Data

[63] Continuation of Ser. No. 843,747, Mar. 25, 1986, abandoned.

[51] Int. Cl.$^4$ ............................................. A61M 25/00
[52] U.S. Cl. ................................................... 604/54
[58] Field of Search ............................ 604/54, 96–101, 604/246, 256; 128/DIG. 25, 341, 343, 344

[56] References Cited

U.S. PATENT DOCUMENTS

| | | | |
|---|---|---|---|
| 1,688,795 | 10/1928 | Aas. | |
| 2,638,093 | 5/1953 | Kulick | 128/133 |
| 2,642,874 | 6/1953 | Keeling | 128/349 |
| 3,094,124 | 6/1963 | Birtwell | 128/348 |
| 3,154,077 | 10/1964 | Cannon | 128/325 |
| 3,181,558 | 5/1965 | Straub | 137/438 |
| 3,331,371 | 7/1967 | Rocchi et al. | 128/349 |
| 3,372,695 | 3/1968 | Beliveau et al. | 128/1 |
| 3,379,197 | 4/1968 | Hayes | 128/349 |
| 3,419,008 | 12/1968 | Plishner | 128/346 |
| 3,495,620 | 2/1970 | Raimondi et al. | 137/529 |
| 3,503,400 | 3/1970 | Osthagen et al. | 128/349 |
| 3,575,158 | 4/1971 | Summers | 128/1 |
| 3,642,004 | 2/1972 | Osthagen et al. | 128/349 R |
| 3,731,670 | 5/1973 | Loe | 128/1 R |
| 3,750,194 | 8/1973 | Summers | 3/1 |
| 3,768,102 | 10/1973 | Kwan-Gett et al. | 3/1 |
| 3,769,981 | 11/1973 | McWhorter et al. | 128/349 B |
| 3,797,478 | 3/1974 | Walsh et al. | 128/1 R |
| 3,805,794 | 4/1974 | Schlesinger | 128/349 R |
| 3,810,259 | 5/1974 | Summers | 3/1 |
| 3,811,450 | 5/1974 | Lord | 128/349 R |
| 3,812,841 | 5/1974 | Isaacson | 128/1 R |
| 3,817,809 | 6/1974 | Dereniuk | 156/296 |

(List continued on next page.)

FOREIGN PATENT DOCUMENTS

| | | |
|---|---|---|
| WO80/01460 | 7/1980 | PCT Int'l Appl. . |
| 273951 | 7/1927 | United Kingdom . |
| 2132091 | 7/1974 | United Kingdom . |

OTHER PUBLICATIONS

Publication of National Technical Service, "Intra-Urethral Prosthetic Sphincter Valve", Leighton, 11/83, 29 pages.

"An Intra-Urethral Silastic Prosthesis", Agarwal et al., (date unknown), 2 pages.

"A Study of Micturition in Patients with Cauda Equina Injury", Scott et al., circa 1973, 5 pages.

Article in *Urology* entitled "Use of Completely Implantable Urethral Catheter in Male Patients with Spinal Cord Injury", Munro & Scott, 11/76, pp. 492–494.

Investigative Urology, entitled "Experiences with a Silastic Spigot as a Replacement for the Urinary Sphincters in Neurogenic Bladder", Conger et al., 11/72, pp. 194–196, 198.

(List continued on next page.)

*Primary Examiner*—Stephen C. Pellegrino
*Attorney, Agent, or Firm*—Peter C. Richardson; Lawrence C. Akers; Gezina Holtrust

[57] ABSTRACT

A method and apparatus for valving body fluids involving a flexible tubular body with a drainage canal therethrough, including collapsible means for blocking the passageway and thereby preventing the flow of urine. The length of the device is such that one end protrudes into the bladder and the other end terminates interior of the meatus. The device includes a means for anchoring to secure it in place and a plug device for deflating and releasing the anchoring means and for collapsing the blocking means to facilitate removal of the device from the body. The device is manually actuable to an open position and means are provided to delay the closing of the device for a sufficient period of time to allow voiding of the bladder. The collapsible and expandable nature of the device facilitates its insertion and removal, particularly while passing through areas of restricted diameter.

11 Claims, 3 Drawing Sheets

U.S. PATENT DOCUMENTS

| | | | |
|---|---|---|---|
| 3,853,122 | 12/1974 | Strauch et al. | 128/79 |
| 3,903,894 | 9/1975 | Rosen et al. | 128/346 |
| 3,926,175 | 12/1975 | Allen et al. | 128/1 R |
| 3,938,529 | 2/1976 | Gibbons | 128/349 R |
| 3,939,821 | 2/1976 | Roth | 128/1 R |
| 3,977,408 | 8/1976 | MacKew | 128/349 B |
| 3,981,299 | 9/1976 | Murray | 128/349 B |
| 3,995,642 | 12/1976 | Adair | 128/349 R |
| 4,022,216 | 5/1977 | Stevens | 128/349 B |
| 4,024,855 | 5/1977 | Bucalo | 128/1 R |
| 4,026,298 | 5/1977 | Grauz | 604/256 X |
| 4,056,095 | 11/1977 | Rey et al. | 128/1 R |
| 4,062,363 | 12/1977 | Bonner, Jr. | 128/349 R |
| 4,102,342 | 7/1978 | Akiyama et al. | 128/325 |
| 4,140,127 | 2/1979 | Cianci et al. | 128/349 R |
| 4,148,319 | 4/1979 | Kasper et al. | 128/349 B |
| 4,155,364 | 5/1979 | Boxer | 128/349 B |
| 4,166,468 | 9/1979 | Haynie | 604/256 X |
| 4,225,979 | 10/1980 | Rey et al. | 3/1 |
| 4,311,659 | 1/1982 | Rey et al. | 264/221 |
| 4,350,161 | 9/1982 | Davis, Jr. | 128/349 BV |
| 4,368,739 | 1/1983 | Nelson, Jr. | 604/54 |
| 4,432,757 | 1/1984 | Davis, Jr. | 604/99 |
| 4,456,011 | 6/1984 | Warnecke | 128/325 |
| 4,457,299 | 7/1984 | Cornwell | 128/1 R |
| 4,497,074 | 2/1985 | Rey et al. | 3/1 |
| 4,549,531 | 10/1985 | Trick | 128/1 R |
| 4,553,533 | 11/1985 | Leighton | 128/1 R |

OTHER PUBLICATIONS

Urology, "A Sound-Catheter", Doroshow, 9/74, pp. 346-347.

"Total Replacement of Ureter by a Scurasil Prosthesis in Pigs", Djurhuus et al., (date unknown), 26 pages.

"Tissue Reaction Six to Eight Months After Total Ureter Substitution with a Scurasil Prosthesis in Pigs", Svensen, (date unknown), 6 pages.

Brochure entitled "Scurasil Artificial Ureter", distributed by Rhodia, Inc., (date unknown), 4 pages.

Brochure entitled "The Rhone-Poulenc Artificial Ureter", distributed by Rhodia, Inc., (date unknown), 1 page.

Brochure entitled "Scurasil Urological Prosthesis", unknown distributor, unknown date, 5 pages.

"A Silicon Polyester Prosthesis for Ureteral Replacement", Stern et al., 1973, pp. 370-373, 375.

Article in Hospital Practice entitled "Operant Conditioning in Gastro-Intestinal Dysfunctions", Schuster, 9/74, pp. 135-143.

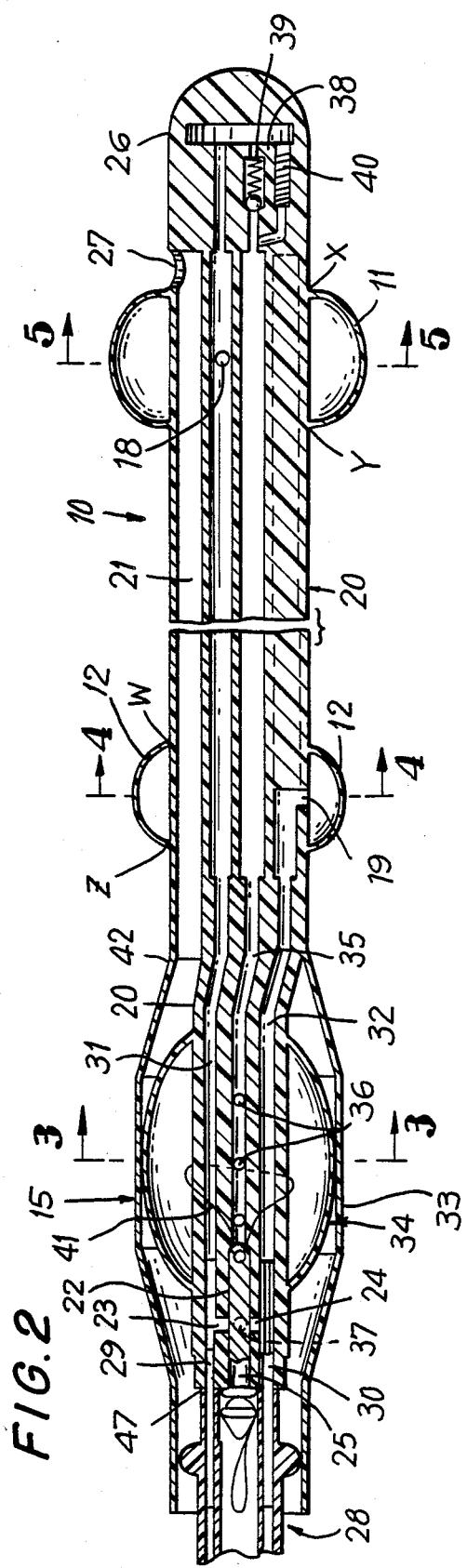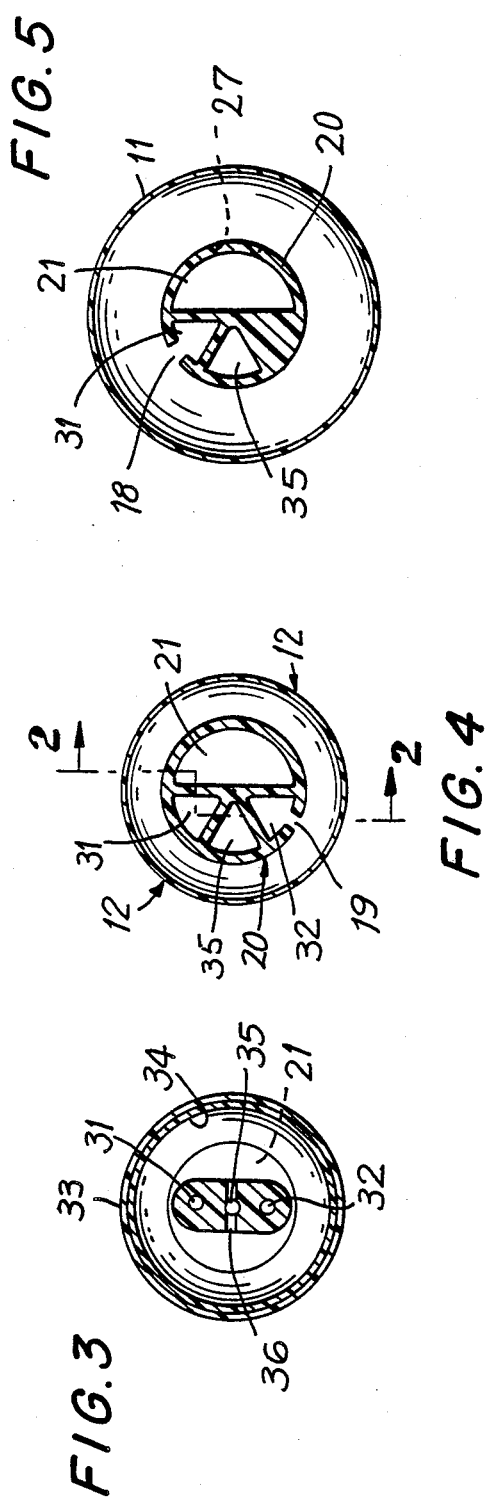

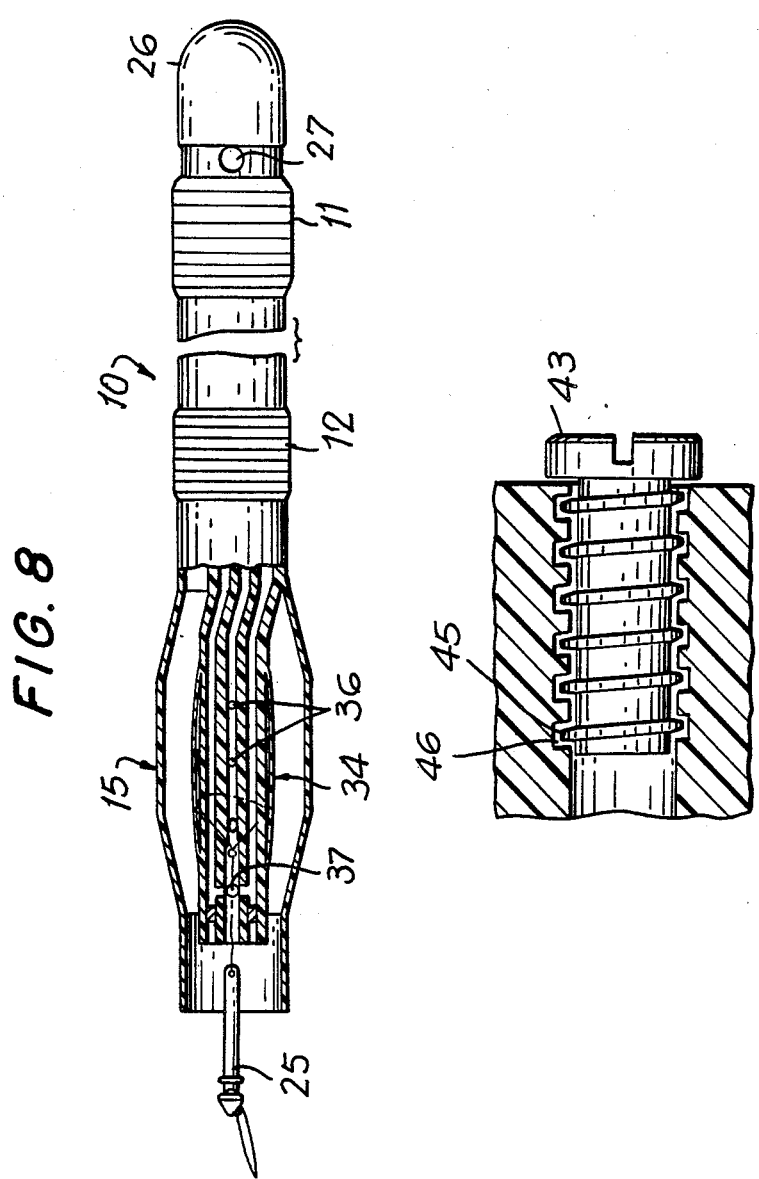
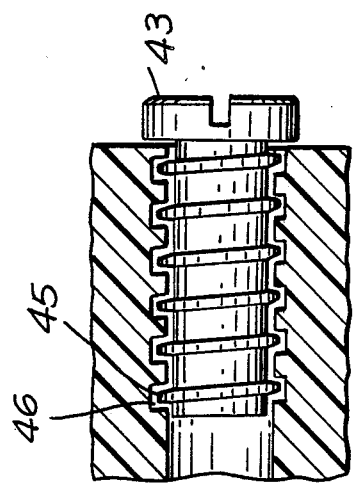
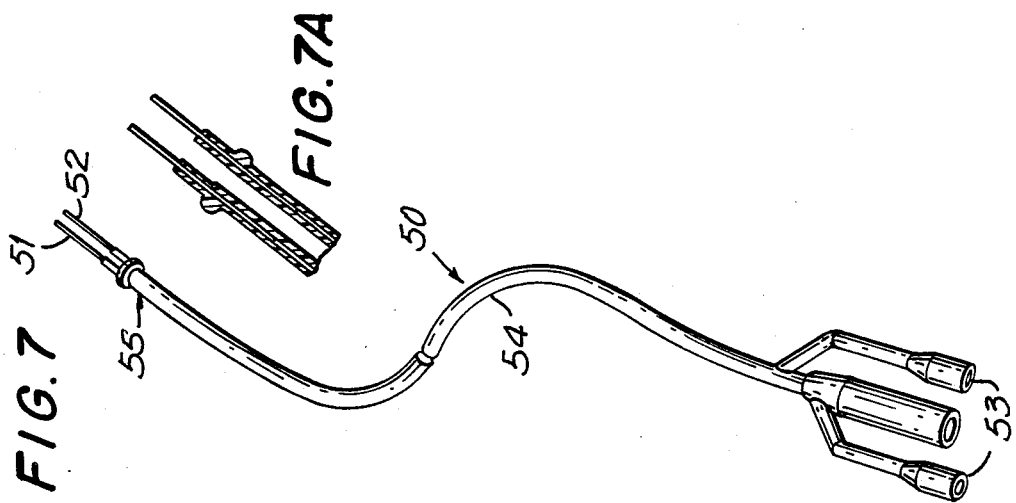

METHOD FOR VALVING BODY FLUIDS

This is a continuation of co-pending application Ser. No. 843,747 filed on 3/25/86, now abandoned.

BACKGROUND OF THE INVENTION

The present invention relates generally to methods and apparatus for valving bodily fluids, such as urine, and particularly to urethral drainage catheters for controlling discharge of fluid from the bladder and more particularly to a device which is completely implanted within the bladder and adjacent portions of the urethra.

FIELD OF THE INVENTION

Urinary incontinence is a serious and long-recognized problem in the medical field, and much effort has been directed to providing devices for handling the problem. The number of patents granted in this field are evidence of such efforts.

Urinary incontinence is the inability to voluntarily control the elimination function of the bladder. This problem can result from numerous causes, including old age, disease, trauma, or some form of neurological dysfunction, and the problem is generally incurable. The patient suffering from urinary incontinence may experience embarrassment, discomfort, and loss of self-esteem. In addition, normal human activity may be severely limited.

Attempts to alleviate this problem have generally involved either external or external/internal devices. Examples of external devices are adult diapers and urine alarms. External/internal devices such as urinary catheters have also been studied. However, such catheters have a limited indwelling life because of the likely onset of serious urethral infections. The operation of such devices is also severely complicated by the very limited diameter of the urethra. These and other complications have made elusive the search for an indwelling urine control device that achieves comfortable, convenient and relatively "normal" bladder control for the incontinent patient.

DESCRIPTION OF THE RELATED ART

Numerous devices have been developed to facilitate the controlled discharge of the urinary bladder, one of the most common being a urethral catheter extending from the bladder, through the entire urethral tract, to the exterior of the body. The catheter is ordinarily inserted into the bladder and retained in position by inflatable cuffs or balloons. A drainage passageway extends the length of the catheter, allowing urine to flow from the bladder to the atmosphere. The drainage passageway may, alternatively, be connected to a collector bag or include a shut-off valve for controlling the passage of urine. U.S. Pat. Nos. 3,642,004 ("Osthagen"), 3,811,450 ("Lord"), and 4,022,216 ("Stevens") are representative of such devices.

The Osthagen, Lord, and Stevens devices have numerous well-known disadvantages, not the least of which is susceptibility to infection. The protruding catheter provides an ideal path for migration of bacteria into the bladder, possibly resulting in extreme complications. Further, the use of collector bags can be both uncomfortable and embarrassing, adversely affecting the wearer's psyche. Finally, use of devices which extend beyond the urethra restricts or prohibits normal activities.

Another approach to the problem of controlling urinary incontinence has been to provide a means for constricting the urethra to block the flow of urine, with the capability of selectively releasing the constriction to allow voiding of the bladder. Such devices are described in U.S. Pat. Nos. 3,939,821 ("Roth") and 3,750,194 ("Summers"). The most common problems associated with the use of a constricting device are impaired circulation, edema, and urethral diverticulum.

Still other methods have been developed to control urinary incontinence by using completely indwelling devices. U.S. Pat. Nos. 3,768,102 ("Kwan-Gett") and 3,797,478 ("Walsh") describe devices which rely on normal voiding pressure being exerted by the wearer to overcome a threshold resistance and start the flow of urine. The devices automatically return to a closed state upon evacuation of the bladder. Another such device is shown in Application Ser. No. 6-550,040, filed by Stephen B. Leighton ("Leighton").

Other indwelling urethral catheters have incorporated valves which are actuated by external forces. U.S. Pat. No. 3,812,841 to Isaacson ("Isaacson") shows a urethral valve which is implanted in the urethra at its point of entry into the bladder. Inflatable collars hold the structure in place while a valve internal to the device prevents the flow of urine through the drainage canal. The valve is magnetic in nature and responds to a magnetic field generated at the exterior of the body. The external field causes the valve to open, thus allowing the bladder to be voided through the urethra, and removal of the field then allows the valve to return to a closed position. The numerous mechanical parts of the Isaacson valve increase the possibility of malfunction of the unit and consequential repair or replacement. Further, the physical size and relative inability of the catheter to collapse, being of "slightly flexible deformable plastic" and sufficiently large to obstruct the urethra near the bladder, present extreme difficulties in insertion and removal.

U.S. Pat. Nos. 4,350,161 and 4,432,757, both to Davis, Jr. ("Davis") show an indwelling urethral catheter used by males which is secured in the bladder by a Foley-type balloon and which extends the length of the urethra to the penile urethra. A valve is mounted at the distal end of the catheter and is normally biased to a closed position. The valve is actuable to an open position by external hand manipulation of the penis. Although the Davis catheter does not extend to the penile meatus, it occupies a significant portion of the penile urethra. Such a position reduces the length of urethra which is subject to the normal flushing of urine and may invite migratory infections. Further, location of the distal end of the catheter and the valve in the penile urethra may result in considerable discomfort upon expansion and contraction of the penis, as upon erection. Finally, as in Isaacson, the rigid valve structure can be a source of considerable discomfort and trauma both in insertion and removal and during normal usage.

One object of the present invention is to overcome many of the above-mentioned drawbacks by providing a manually actuated urinary continence device which is completely indwelling within the urinary tract, thereby reducing the possibility of infection associated with many of the prior devices.

SUMMARY OF THE INVENTION

According to the present invention, a method and apparatus for valving bodily fluids may involve a device which is intended to be located in the urethra between the bladder and the penile meatus. The device does not extend outside the penis and thereby may provide protection against infection. The device is secured in place by means of inflatable balloons located generally in the bladder and in the proximal urethra area, inhibiting significant movement along the urethra in either direction.

A drainage passageway extends the length of the device and facilitates evacuation of the bladder. The passageway is blocked by a collapsible valve which is manually actuable to an open position. Once opened, the valve remains open for a short period of time to allow evacuation of the bladder and, after the delay, automatically returns to its closed position.

The valve is collapsible from its normal shape to allow ease of insertion through areas of restricted diameter in the urethra. When properly positioned, the valve resumes its normal shape, increasing its cross-sectional area and, thus, the flow area therethrough.

An insertion tool attaches to the device for insertion into the patient's urethra, inflating the balloons which hold the device in place, thereby inflating the collapsible valve. Inflation passages in the insertion tool communicate with the device via self-sealing valves, or septums. Following insertion of the device and inflation of the balloons and collapsible valve, the insertion tool is withdrawn from the urethra, leaving the device in place. The self-sealing valves prevent deflation of the balloons and valve upon withdrawal of the insertion tool.

The device is removable from the urethra generally by means of a cystoscope or similar device. A plug at the distal end of the device is grasped by the withdrawal tool and pulled, allowing deflation of the balloons and collapsible valve and providing a means for withdrawing the device from the urethra. Alternatively, a monofilament cord, or similar device, may be attached to the plug and allowed to extend outside the urethra to be grasped and pulled to deflate the balloons and valve and facilitate removal of the device.

BRIEF DESCRIPTION OF THE DRAWINGS

FIG. 2 is a view of the device of FIG. 1 as sectioned along its longitudinal axis showing the balloons and valve in inflated conditions with the insertion/inflation tool attached.

FIG. 3 is a cross-section of the device taken along lines 3—3 in FIG. 2.

FIG. 4 is a cross-section of the device taken along lines 4—4 in FIG. 2.

FIG. 5 is a cross-section of the device taken along lines 5—5 in FIG. 2.

FIG. 6 is an enlarged, longitudinal section view of bleed-back device 40 shown in FIG. 2.

FIG. 7 is a perspective view of one embodiment of an insertion tool that may be used with the present invention.

FIG. 8 is a view of the device as sectioned along its longitudinal axis showing the plug removed and the balloons and valve in deflated conditions.

DETAILED DESCRIPTION

Figure 1:
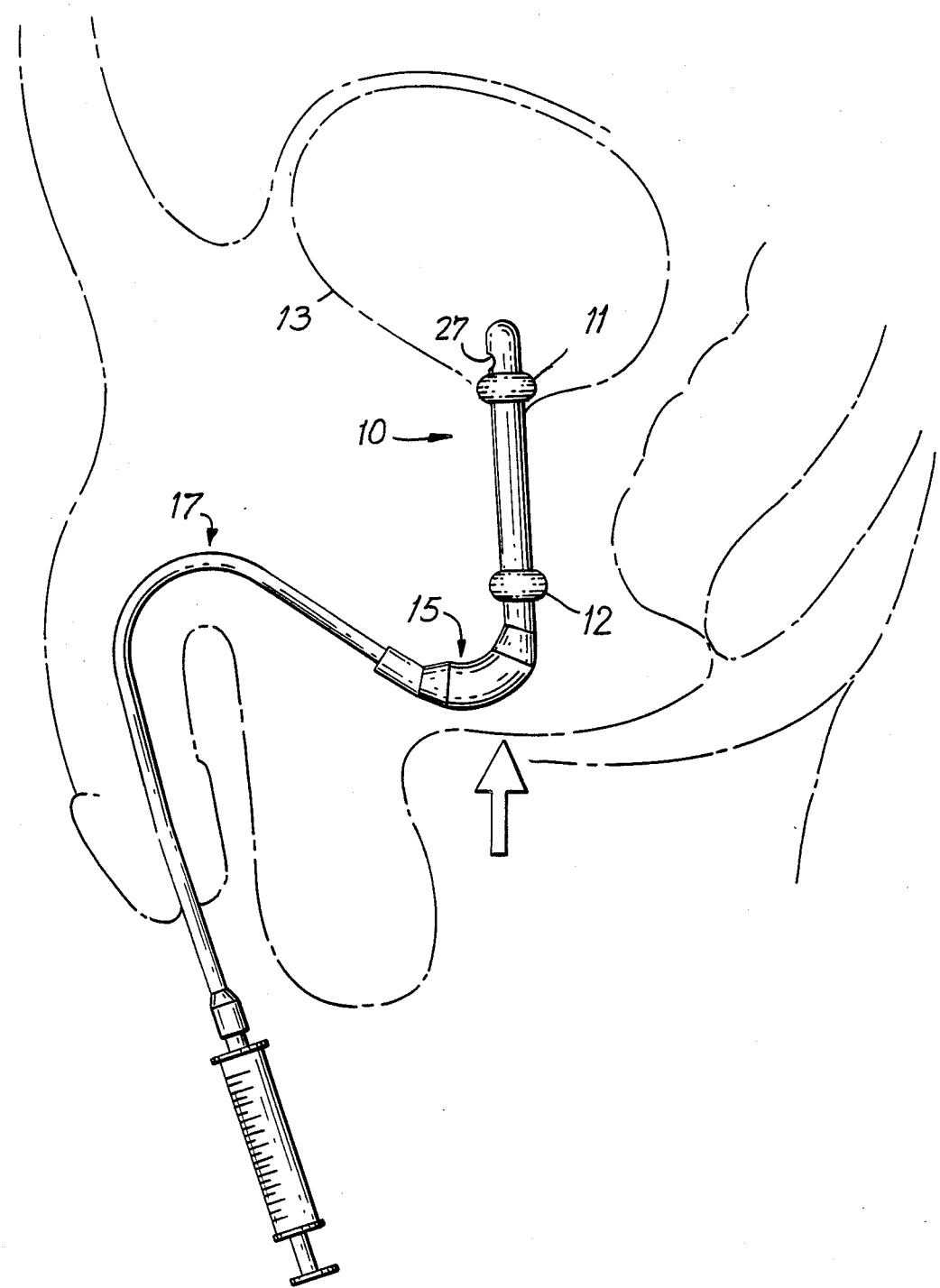
FIG. 1 illustrates one preferred embodiment of the present invention as it is positioned in the male urethra with the insertion/inflation tool attached.

FIG. 1 illustrates one embodiment of a device 10 of the present invention positioned within the male urethra 17. Inflatable balloons 11 and 12, located within the bladder 13 and the proximal urethra, respectively, anchor the device 10 in place and secure it against significant movement in either direction. A valve assembly 15 is located below inflatable balloon 12 and, when inflated, obstructs the urinary passage 21 (shown in FIG. 2) within the device 10 to prevent the flow of urine from the bladder 13.

The location of the valve assembly 15 is variable, as is the overall length of the device 10, and FIG. 1 illustrates only one embodiment of the invention, that being the preferred embodiment. In this embodiment, as noted above, inflatable balloons 11 and 12 are located in the bladder and proximal urethra and valve assembly 15 is located in the region of the bulbous urethra.

Referring now to FIG. 2, a preferred embodiment of device 10 generally comprises a tubular body 20 with a longitudinal passageway, or lumen, 21 therein. Inflatable balloons 11 and 12 serve to anchor the device 10 within the bladder and urethra and valve assembly 15 controls the flow of urine through passageway 21.

Tubular body 20 is preferably formed of a flexible material, for example, silicone, to facilitate insertion and removal of the device as well as to decrease the discomfort normally associated with the use of such a device. The material should preferably be biocompatible so as not to cause complications within the urinary tract. The diameter of tubular body 20 is very restricted so that it will easily pass through restricted regions of the urethra.

As noted above, tubular body 20 contains a passageway, or lumen, 21 extending longitudinally the length of device 10. A port 27, located at proximal end 26 of device 10, allows for the entry of urine into passageway 21.

Located adjacent port 27 is inflatable balloon 11. The balloon 11 is formed from a resilient and stretchable material and comprises a tube concentric about body 20 with a diameter approximating that of body 20. The upper and lower ends of balloon 11 are affixed at points X and Y to the exterior surface of body 20 by means of a silicone adhesive, or similar means. The central portion of balloon 11 is thus expandable in response to internal pressurization to form a circumferential barrier, or cuff, about tubular body 20. Balloon-filling port 18 penetrates the side wall of body 20 and is longitudinally situated between the upper and lower peripheries of balloon 11, points X and Y. Within tubular body 20 and in communication with port 18 is a second longitudinal passageway, or lumen, 31, which will be more fully described below.

Spaced longitudinally from balloon 11 is fixation balloon 12. Balloon 12 is formed in a manner similar to that of balloon 11 and is affixed in like manner to the exterior of body 20 at points W and Z, thus forming a second circumferential barrier, or cuff. Balloon-filling port 19, as in the case of port 18, penetrates the side wall of body 20 and is longitudinally situated between the upper and lower peripheries of fixation balloon 12, points W and Z. Contained within tubular body 20 and in communication with port 19 is a third longitudinal passageway 32, which will be more fully explained below.

Near distal end 28 of device 10 is a collapsible valve assembly 15. The assembly 15 generally comprises an inflatable bulb 34, ports 36, and flexible sheath 33. The sheath 33 is formed from a semi-resilient material similar to that of body 20 and balloons 11 and 12 and is of a tubular construction. The sheath 33 fits over the distal end 28 of tubular body 20, forming an annular space therebetween, and its proximal end 42 is permanently affixed about the circumference of body 20 using a silicone adhesive or similar means.

Sheath 33 is pre-formed in a shape resembling an ellipse so that its diameter at its central region is greater than its diameter at either end. This is most easily seen in FIGS. 2 and 8. When in its normal condition, the sheath 33 forms an annular space about the body 20 which is typically larger in cross-sectional flow area than the annular space defined when the sheath 33 is collapsed against the body 20, as when passing through areas of restricted diameter.

Contained within the annular space formed between body 20 and sheath 33 is an inflatable bulb 34. The bulb 34 is formed in like manner to balloons 11 and 12 and is affixed to the exterior of the body 20 in a similar manner. The valve ports 36 penetrate the side wall of tubular body 20 and provide fluid communication between the interior of bulb 34 and valve control passage 35, which will be more fully explained below.

FIG. 2 illustrates the locations and interconnections of passages 21, 31, 32, and 35. Longitudinal passageway 21 extends from port 27 at proximal end 26 of device 10, along the longitudinal axis of body 20 to the proximal end 42 of sheath 33. The annulus formed between the sheath 33 and tubular body 20 creates an extension of urinary passageway 21 from the proximal end 42 of sheath 33 to the distal end 28 of device 10. Balloon-filling passage 31 extends along the longitudinal axis of body 20 from proximal end 26 to distal end 28 of device 10. As explained above, passage 31 is connected to the interior of inflatable balloon 11 by means of port 18. At its proximal end, passage 31 is connected to flow control mechanism 38, the structure of which will be more fully explained below. Balloon-filling passage 32 is also situated along the longitudinal axis of body 20 and extends from fixation balloon 12 to distal end 28. Again as explained above, the passage 32 is connected to the interior of fixation balloon 12 by means of the port 19. Valve control passage 35 is situated along the longitudinal axis of body 20 and extends from proximal end 26 to chamber 22 near the distal end 28. At its proximal end, passage 35 is connected to flow control mechanism 38. Ports 36 provide fluid connection between passage 35 and the interior of inflatable bulb 34.

Inflatable bulb 34 in its inflated condition presses against sheath 33, as shown in FIGS. 2 and 3. The body 20 is substantially oval-shaped in its cross-section and contains passages 31, 32, and 35. A port 36, illustrated in FIG. 3, connects valve control passage 35 with the interior of inflatable bulb 34.

Referring to FIG. 4, the body 20 is generally circular in cross-section in the area of fixation balloon 12 and contains the semi-circular urinary passageway 21 and the pie-shaped balloon-filling passages 31 and 32, and valve control passage 35. The general shape and configuration of the various passages provides for optimal use of the restricted diameter of body 20; however, other shapes and arrangements may be used. It is preferred that the diameter of body 20 be minimized for reasons which will be more fully explained below. The port 19 connects the balloon-filling passage 32 with the interior of fixation balloon 12.

The portion of body 20 near the balloon 11 contains urinary passageway 21, balloon-filling passage 31, and valve control passage 35, as shown in FIG. 5. Port 18 connects balloon-filling passage 31 and the interior of inflatable balloon 11. The balloons 12 and 11 are concentric with the circumference of body 20. FIG. 3 illustrates that both inflation bulb 34 and sheath 33 are circumferential about body 20 and are concentric with one another.

Flow control mechanism 38 is located within tubular body 20 at its proximal end. The mechanism 38 comprises two primary elements. A check valve 39 is connected at one end to balloon-filling passage 31 and at its other end to valve control passage 35. Check valve 39 allows one-way flow of fluid from passage 35 into passage 31 but will not allow fluid to flow from passage 31 to passage 35. Bleed-back device 40 is connected to passages 31 and 35 and is connected in parallel to check valve 39. Bleed-back device 40, as used in one embodiment, is illustrated in FIG. 6 as a screw 43 loosely threaded into port 44. Threads 46 in port 44 generally provide a loose fit with threads 45 on screw 43, resulting in a helical flow path from passage 31 to passage 35. The operation of flow control mechanism 38 will be explained in detail below.

The chamber 22 is located at distal end 28 of device 10 and is generally cylindrical in shape. The cylindrical chamber is formed along the longitudinal axis of body 20 and extends from adjacent inflatable bulb 34 to the distal end 47 of tubular body 20. At one end, chamber 22 is open to the exterior of body 20 and, at its other end, chamber 22 is connected to passages 31 and 32 by means of vents 23 and 24, respectively. Passage 35 terminates, at its distal end, in chamber 22. Chamber 22 is configured to accept a generally cylindrical plug 25. Plug 25 fits within chamber 22 to obstruct vents 23 and 24 and the distal end of passage 35. The plug 25 may be attached to body 20 by means of a suture 41 looped about the circumference of body 20, as shown in FIG. 2.

Also located at distal end 28 of device 10 are self-sealing valves, or septums, 29 and 30. As explained above, balloon-filling passages 31 and 32 extend along the longitudinal axis of body 20 to distal end 47 of body 20. Self-sealing valves 29 and 30 may be formed from any resilient substance which may be penetrated by a needle and which will collapse upon itself upon withdrawal of the needle. In the preferred embodiment, that substance is silicone. Valves 29 and 30 generally resemble silicone plugs located within the distal ends of balloon-filling passages 31 and 32.

The operation of devices 10 may be substantially as follows:

Prior to insertion into the urethra, device 10, representing a preferred embodiment of the present invention, is in a completely deflated state. Balloons 11 and 12 and bulb 34 are collapsed against the exterior of body 20. Sheath 33 is in its normal shape, bulged away from body 20. Plug 25 is inserted into chamber 22, obstructing vents 23 and 24, and passageway 35, preventing flow of fluid therebetween.

Insertion tool 50, illustrated in FIG. 7, is attached to the distal end 28 of device 10. Needles 51 and 52 penetrate self-sealing valves 29 and 30, and sleeve 55 on the distal end 28 of device 10 fits snugly around the proximal end 55 of insertion tool 50. Insertion tool 50 is generally in the configuration of a Foley-type catheter, with certain important modifications, and is made of a flexible material such as that used in device 10. Although the Foley-type catheter is generally known to those skilled in the art, the tool 50 departs from construction of the typical Foley-type catheter in certain important ways, particularly in the arrangement of the proximal end 55.

After insertion tool 50 has been attached to device 10, the device is guided into and along the urethra into its proper position. Because of the small diameter of device 10 and the collapsible nature of balloons 11 and 12 and valve assembly 15 (including sheath 33 and bulb 34), the device is easily maneuverable through relatively narrow areas commonly found in the urethra, especially the urethral meatus. Sheath 33, being of a flexible material, collapses from its normal shape to lay against body 20 and substantially eliminate the trauma normally associated with insertion of intraurethral devices.

Once it is properly positioned, device 10 is completely within the urethra, while the insertion tool 50 protrudes therefrom. Proximal end 26 of device 10 has protruded into the bladder. Valve assembly 15 and sheath 33, when the device 10 is properly positioned, are located in a generally enlarged area of the urethra, and sheath 33 assumes its pre-formed, bulging shape, thus enlarging the annular space formed between sheath 33 and body 20, resulting in an enlarged flow area in valve assembly 15.

A syringe generally used with Foley-type catheters is attached to the insertion tool at points 53 and inflation fluid is injected through self-sealing valves 29 and 30. A radiopaque fluid is preferred to facilitate post-insertion x-ray and viewing of the device while in the body. For example, Hypaque-25 or Renografin-60, aqueous dilutions thereof, or equivalents, may be used as the radiopaque fluid. Alternatively, a relatively compressible fluid may be employed in an alternate embodiment.

After the device 10 has been properly positioned within the urethra with its proximal end 26 protruding into the bladder, inflation fluid is injected through self-sealing valve 29, along passageway 31, and into balloon 11, located within the bladder. As balloon 11 is inflated, a differential pressure begins to develop across flow control mechanism 38. Check valve 39 is oriented so as to prevent the flow of fluid from passage 31 into passage 35; however, bleed-back device 40 will allow a gradual helical flow of fluid along threads 45 and 46 from one passage to the other. As a result of the pressure differential across mechanism 38, inflation fluid begins to gradually flow through bleed-back device 40 and into and through valve control passage 35. Fluid continues to flow through ports 36, filling bulb 34 and causing it to begin to expand against sheath 33. Because plug 25 is positioned within chamber 22, obstructing the distal end of passageway 35, fluid cannot escape from valve assembly 15. Sufficient fluid is injected through self-sealing valve 29 and into passage 31 such that, when fluid pressure is equalized between balloon 11 and bulb 34 and flow through bleed-back device 40 ceases, balloon 11 is inflated to secure device 10 within the bladder and bulb 34 is pressed against sheath 33, blocking passage 21.

Because sheath 33 is resistively expandable, it will begin to expand as bulb 34 expands under pressure from the inflation fluid. However, the sheath 33 offers resistance to or bias against continued expansion of bulb 34, creating an effective seal within the annular space between bulb 34 and sheat 33. By varying the volume of inflation fluid injected through self-sealing valve 29, the effectiveness of the seal between sheath 33 and bulb 34 can be varied.

Because the valve 15 operates by radial expansion, a relatively large area of sealing contact between sheath 33 and bulb 34 may be achieved. This large contact area improves the sealing efficiency of the valve 15.

When the predetermined volume of fluid has been injected into balloon 11, a slight pull on the insertion tool serves to seat the device at the bladder neck. This anchoring prevents migration of the device from the bladder. The syringe is then used to inject inflation fluid through self-sealing valve 30, along passage 32, through port 19, and into balloon 12. Sufficient fluid is injected to adequately secure the device 10 in its proper position. Additionally, balloon 12 serves to seal the annular region formed between the tubular body 20 of device 10 and the urethra, thereby helping to prevent leakage of urine along the exterior wall of device 10.

When the device 10 has been properly inflated, the insertion tool is disconnected from the device with a steady pull and is withdrawn from the urethra. As the insertion tool is disconnected from device 10, needles 51 are withdrawn from self-sealing valves 29 and 30 and their self-sealing nature seals the holes created by penetration of the needles. The inflation fluid is thus prevented from escape from device 10.

The seal created between sheath 33 and bulb 34 obstructs longitudinal passageway 21 and prevents the flow of urine from the bladder through the passageway. However, in the event bladder pressure exceeds the inflation fluid pressure at the seal, "leak through" can occur. Indeed, such a capability may be desired in order to signal the need for voiding the bladder. If "leak through" is not desired, pressure at the seal may be increased by injection of a greater volume of inflation fluid. Again, the point at which "leak through" will be allowed can be controlled by the volume of inflation fluid injected.

When voiding of the bladder is desired, device 10 is operated as follows:

Valve assembly 15 is palpated by manually pressing a point external of the body in the area of the assembly. In the preferred embodiment, valve assembly 15 is located near the perineum, as shown in FIG. 1, and upwardly directed manual pressure on the perineum is transmitted via the urethral wall to sheath 33 and bulb 34. Inflation fluid is pumped from bulb 34 through ports 36 and valve control passage 35. Fluid readily flows through check valve 39 and into passage 31.

Because vent 23 is obstructed by plug 25, the fluid is forced into balloon 11, causing it to expand. Balloon 11, therefore, functions as a temporary reservoir for the fluid pumped from bulb 34. As bulb 34 becomes collapsed or deflated, the seal between it and sheath 33 is eliminated, opening the longitudinal passageway 21 and allowing urine to flow from the bladder through the device to the exterior of the body. In addition, because bulb 34 has been deflated and balloon 11 is expanded with filling fluid, a pressure differential is created across bleed-back device 40, causing a gradual flow of fluid to return to bulb 34.

In another embodiment, using a compressible inflation fluid, reservoir 11 may not expand beyond its normal anchoring size, but rather may compress the inflation fluid as it is received. The reduced fluid pressure in bulb 34 will allow it to collapse as above and the increased pressure in reservoir 11, created by the compression of the fluid, will effectuate the differential pressure necessary to cause the gradual flow of fluid from reservoir 11 to bulb 34.

Returning to the illustrated embodiment, this gradual flow continues until the pressure between balloon 11 and bulb 34 is once again equalized. The return of fluid from balloon 11 to bulb 34 through bleed-back device 40 is gradual enough so as to allow ample time for the bladder to void. During normal operation of device 10, fixation balloon 12 is unaffected and maintains its anchoring effect and seal against the urethral wall.

When device 10 is to be removed from the urethra, a cystoscope, or similar tool, is used to pull the plug 25 from its position within chamber 22, as indicated in FIG. 8. Balloons 11 and 12 are emptied through passages 31 and 32, vents 23 and 24 and chamber 22. In addition, inflation fluid contained in bulb 34 is allowed to escape through ports 36, valve control passage 35, and chamber 22. Balloons 11 and 12 and bulb 34 become collapsed and valve assembly 15 becomes readily collapsible, facilitating removal of the device from the urethra. The plug 25 is connected to device 10 by means of a suture 41, or similar connection, and removal of the device from the urethra is accomplished by gripping and pulling on the plug 25 with a cystoscope or similar tool. As was the case on insertion, the collapsible nature of valve assembly 15 and the restricted diameter of tubular body 20 allow the passing of the device through various restricted areas along the urethra.

Although the above description describes details of a preferred embodiment of the present invention, it will be understood by those skilled in the art that numerous other embodiments and applications of the invention exist. Although in many such applications, all of the advantages of the illustrated embodiment may not be achieved, certain desirable attributes may be attainable. For example, the length of the device may be varied for specific applications and the device need not be restricted to use in the male urethra, or even to use in humans. Further, the sheath 33 may be omitted in certain situations, in which case inflatable bulb 34 seals against the wall of the urethra with the urinary passageway 21 terminating above inflatable bulb 34. Still further, use of the invention will not require two balloons in certain applications; for example, where migration must be prevented in only one direction or where one inflatable balloon will prevent movement in more than one direction. Indeed, inflatable circumferential balloons 11 and 12 may each be replaced with one or more inflatable balloons situated about the circumference of the catheter body. Flow control mechanism 38 may assume numerous configurations which achieve immediate flow of fluid in one direction and delayed or gradual flow of fluid in the opposite direction.

The collapsible valve of the invention will find use not only in embodiments such as the urethral device described herein but also in any indwelling situation where a collapsible, expandable valve is desired to control the flow of body fluids. Such situations could include catheters for use in blood vessels as well as devices for controllably blocking other body passages, e.g., esophagus or colon.

In the embodiment described herein, the collapsible valve is small enough to pass through restricted areas of the urethra, particularly the penile meatus, without significant trauma, and yet, when it is properly positioned in the bulbous urethra, it may be expanded to a size which is easily palpable but much too large a diameter to ever pass through such restricted areas. Likewise, in other embodiments and applications, the collapsible and expandable nature of the valve provides easy passage and positioning as well as expansion to an effective functioning size once positioned. The actual mechanism for operation of the valve once in position is relatively unimportant as long as the collapsing and expanding features of the valve structure, as a whole, are not compromised. For example, other means for collapsing, expanding, opening or closing the valve during normal use could utilize magnetic actuators, mechanical actuators, contracting and expanding fluids, compressible fluids, or other effective devices.

It is to be understood that the invention is to be limited only by the appended claims.

What is claimed is:

1. A method for achieving urinary continence, comprising the steps of:
   inserting a collapsible valving member into a first position in the urethra proximate the bladder, the valving member including means for directing urine flow from the bladder through an expanding valve;
   expanding said valve outwardly when said valving member is in said first position so as to substantially halt the flow of urine from the bladder; and
   selectively contracting said valve to allow urination.

2. The method of claim 1 wherein the step of contracting said valving member includes the step of ducting fluid to a holding reservoir.

3. The method of claim 1, including the step of allowing said valving member to gradually expand after being selectively contracted.

4. The method of claim 1, including the step of inserting said valving member such that said member is spaced inwardly from the meatus.

5. The method of claim 1, including the step of anchoring said member in said first position by inflating a cuff, connected to said member, in the bladder.

6. The method of claim 5, including the step of removing said member by removing a plug and allowing said cuff to deflate.

7. The method of claim 1, including the steps of providing a sheath surrounding said valving member and expanding said member until said sheath limits the further expansion of said member.

8. A method for achieving urinary continence, comprising the steps of:
   collapsing a valve member from its normal shape for insertion through areas of restricted diameter, the valve member being coupled to a longitudinal body having a flow passage;
   inserting said valve member and said body into a position in the urethra proximate the bladder, the body protruding into the bladder;
   allowing an outer portion of said valve member to automatically expand to its normal shape to increase the flow area therethrough;
   expanding an inner portion of said valve member against the outer portion so as to substantially halt the flow of urine through the flow passage; and
   selectively compressing said inner portion of said valve member to allow the flow of urine from the bladder through the flow passage.

9. The method of claim 8, wherein said step of selectively compressing comprises the step of:
   palpating said valve member to its normal shape to allow the flow of urine past said member.

10. The method of claim 8 further comprising the step of:
   automatically re-expanding said valve member after urination.

11. The method of claim 8, wherein said step of selectively compressing is accomplished from outside the urethra.

* * * * *